(12) United States Patent
He et al.

(10) Patent No.: US 8,981,048 B2
(45) Date of Patent: Mar. 17, 2015

(54) CASPOFUNGIN ANALOG, AND PREPARATION METHOD AND USES THEREOF

(75) Inventors: Bingming He, Shanghai (CN); Ming Li, Shanghai (CN); Zhijun Tang, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/884,775

(22) PCT Filed: Nov. 10, 2011

(86) PCT No.: PCT/CN2011/082023
§ 371 (c)(1),
(2), (4) Date: May 10, 2013

(87) PCT Pub. No.: WO2012/062214
PCT Pub. Date: May 18, 2012

(65) Prior Publication Data
US 2013/0225482 A1    Aug. 29, 2013

(30) Foreign Application Priority Data
Nov. 10, 2010   (CN) .......................... 2010 1 0539239

(51) Int. Cl.
C07K 7/56      (2006.01)
A61K 38/12     (2006.01)
A61K 38/00     (2006.01)

(52) U.S. Cl.
CPC . *C07K 7/56* (2013.01); *A61K 38/12* (2013.01); *A61K 38/00* (2013.01)
USPC ............. 530/317; 514/2.9; 514/3.6; 514/21.1

(58) Field of Classification Search
None
See application file for complete search history.

(56) References Cited

U.S. PATENT DOCUMENTS

2010/0168415 A1*   7/2010  Lee et al. ...................... 540/460

FOREIGN PATENT DOCUMENTS

| CN | 101648994 A | 2/2010 |
| WO | WO 9624613 A1 * | 8/1996 |
| WO | WO 02083713 A2 * | 10/2002 |

OTHER PUBLICATIONS

Machine translation of CN 101648994 (A) (Feb. 17, 2010).*
International Search Report from Application PCT/CN2011/082023, dated Feb. 16, 2012, 3 pages.

* cited by examiner

*Primary Examiner* — Jeffrey E Russel
(74) *Attorney, Agent, or Firm* — Hamre, Schumann, Mueller & Larson, P.C.

(57) ABSTRACT

Disclosed are a caspofungin analog, and a preparation method and applications thereof. The caspofungin analog has a structure as represented in Formula 3.

15 Claims, No Drawings

CASPOFUNGIN ANALOG, AND PREPARATION METHOD AND USES THEREOF

TECHNICAL FIELD

The present invention relates to the field of organic chemistry, particularly to a caspofungin analog, and the preparation method as well as the use thereof.

BACKGROUND

In 1974, it was discovered that echinocandin compounds possess excellent antibacterial activity. Thereafter, many semisynthetic echinocandin compounds have been studied for their pharmacologic activities. In 2001, caspofungin was approved by US FDA, which represents the landmark for the research of antifungal medicaments. Caspofungin, the chemical structure of which is shown by Formula 1, represents a broad-spectrum and low-toxic medicament with unique action site:

1

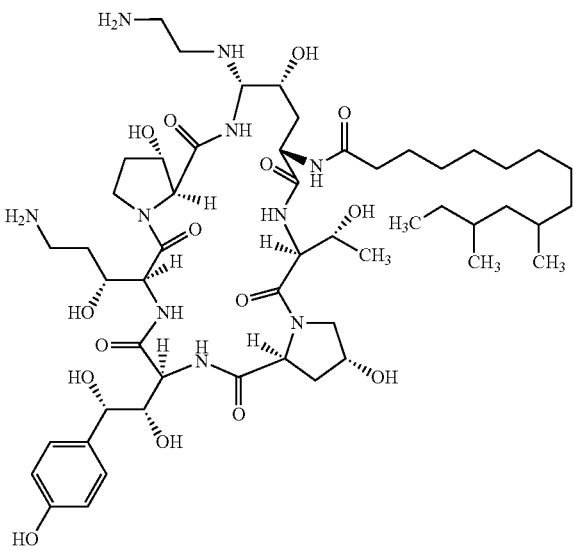

Caspofungin analogs and the preparation of Caspofungin have been described in WO94/21677, EP620232, WO96/24613, U.S. Pat. No. 5,552,521, WO97/47645, U.S. Pat. No. 5,936,062, WO02/083713, J. Org. Chem., 2007, 72, 2335-2343, CN101792486A, CN 101648994A, WO2010008493A2, US2010168415A1, EP1785432, and WO2010064219A1.

In WO94/21677 and EP 620232, the method for synthesizing and purifying caspofungin has been disclosed, comprising the following steps: Pneumocandin $B_0$ as the starting material reacts with alkyl thiol or aryl thiol, the resulting product is oxidized to obtain the sulfone intermediate, and then the sulfone intermediate reacts with amines in anhydrous non-proton solvent to obtain caspofungin, which was purified by chromatography.

According to WO96/24613 and U.S. Pat. No. 5,552,521, primary amide group in Pneumocandin $B_0$ is reduced to amine group (47% of yield), and then the resulting product reacts with thiophenol and ethylenediamine in turn to obtain caspofungin.

In WO97/47645, U.S. Pat. No. 5,936,062 and J. Org. Chem., 2007, 72, 2335-2343, two stereoselective methods for preparing caspofungin from Pneumocandin $B_0$ have been reported. In the first method, benzyl borate is used as protective group, amide group in Pneumocandin $B_0$ is reduced to amine group, and then the resulting product reacts with thiophenol and ethylenediamine in turn to obtain caspofungin; in the second method, Pneumocandin $B_0$ as the starting material reacts with thiophenol, the resulting product is protected by benzyl borate, the amide group in Pneumocandin $B_0$ is reduced to amine group, and then the resulting product reacts with ethylenediamine to obtain caspofungin.

In CN101792486A and CN 101648994A, a method has been disclosed, comprising the following steps: Pneumocandin $B_0$ as the starting material reacts with ethylenediamine under the protection of phenyl borate, and then the amide group in the resulting intermediate is reduced to amine group to obtain caspofungin.

In WO02/083713, US2010168415A1, EP1785432, WO2010064219A1, a method has been disclosed, comprising the following steps: the intermediate of Pneumocandin $B_0$ containing cyano is prepared, and then the intermediate is reduced by using hydrogen to obtain caspofungin.

According to WO2010008493A2, Pneumocandin $B_0$ as the starting material reacts with 4-methoxy thiophenol, the resulting product is protected by phenyl borate, the amide group in Pneumocandin $B_0$ is reduced to amine group under the condition of dehydration by 3A molecular sieve, and then the resulting product reacts with ethylenediamine to obtain caspofungin.

However, for the yield, purity, stability and waste, none of the disclosed methods is the optimal method for industrialization. The cost for industrialization will be greatly increased due to the repeated use of chromatographic column, thus resulting in great amount of waste. Some methods must be conducted under strict anhydrous conditions (such as, dehydration by 3 A molecular sieve). Most of the methods use thiophenol with odor and high toxicity, are difficult to be operated, harmful to the operator and severely pollute the environment. Additionally, isomers are inevitably produced during the preparation of Pneumocandin $B_0$ containing cyano, the stereoselectivity and yield are not high, and expensive metals are used as catalysts, thereby resulting in high cost for industrialization. Therefore, it is urgent to develop a method for preparing caspofungin which is suitable for industrialization.

SUMMARY OF THE INVENTION

The subject of the present invention is to provide a caspofungin analog.

Another subject of the present invention is to provide a preparation method for the caspofungin analog.

Another subject of the present invention is to provide uses of the caspofungin analog.

In the first aspect of the invention, the compound of Formula 3 or the pharmaceutically acceptable salts thereof is provided,

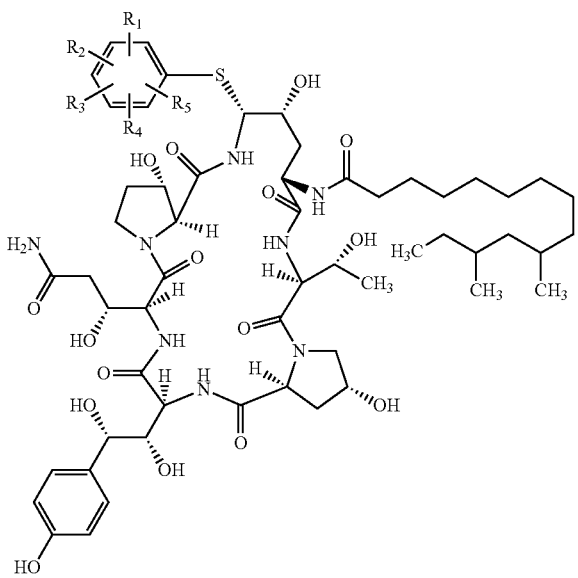

3

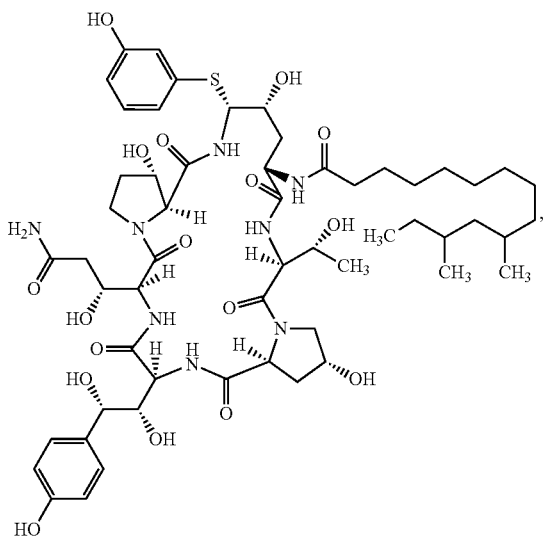

3b

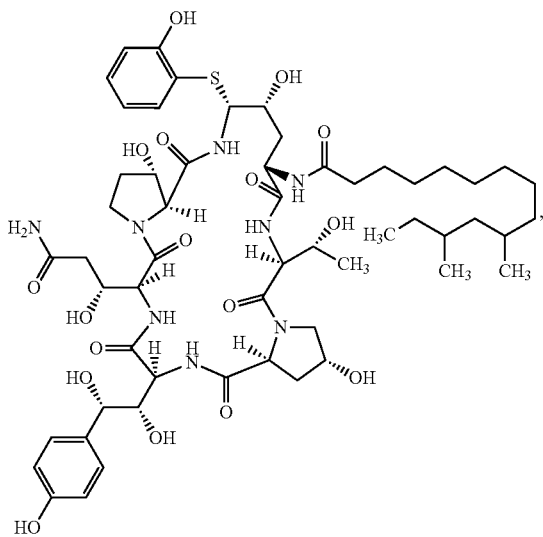

3c wherein $R_1$ is selected from hydroxy, benzyloxy, phenoxy, or substituted phenoxy, or substituted benzyloxy; $R_2$, $R_3$, $R_4$, $R_5$ is selected from hydrogen, C1-C6 alkyl, C1-C6 alkoxy, hydroxyl, or benzyloxyphenyl, substituted benzyloxyphenyl, nitro, fluorine, chlorine, bromine, iodine, respectively.

Preferably, $R_1$ is selected from hydroxy, benzyloxy, phenoxy, or substituted phenoxy; $R_2$, $R_3$, $R_4$, $R_5$ is selected from hydrogen, C1-C4 alkyl, C1-C4 alkoxy, hydroxyl, bromine or nitro.

More preferably, $R_1$ is selected from hydroxy; $R_2$, $R_3$, $R_4$, $R_5$ is selected from hydrogen, methyl, or hydroxyl.

In another preferred example, the compound is the compound of Formula 3a, 3b, 3c, 3d, or 3e:

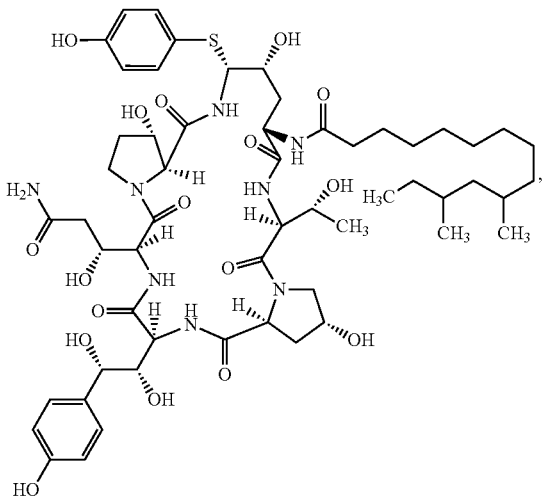

3a

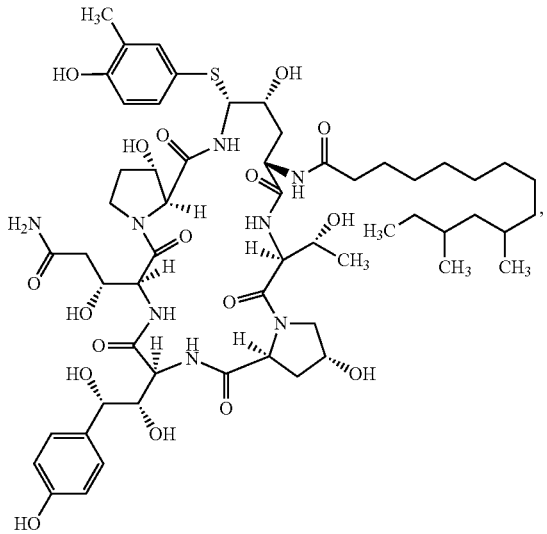

3d

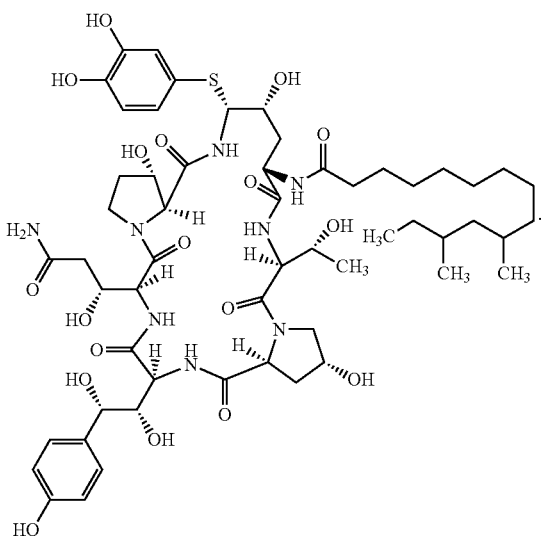 [SMILES: CCC(C)CC(C)CCCCCCCCC(=O)N[C@H]1C[C@@H](O)[C@@H](Sc2ccc(O)cc2)NC(=O)[C@@H]2[C@@H](O)CCN2C(=O)[C@H]([C@H](O)CC(N)=O)NC(=O)[C@H]([C@H](O)[C@@H](O)c2ccc(O)cc2)NC(=O)[C@@H]2C[C@@H](O)CN2C(=O)[C@H]([C@@H](C)O)NC1=O]

3e

In another preferred example, the compound is the compound of Formula 3a.

In the second aspect of the invention, a preparation method for the compound of Formula 3 or the pharmaceutically acceptable salts thereof is provided, said method comprising the following step:

mixing the compound of Formula 2 with a strong leaving-group compound, thereby obtaining the compound of Formula 3,

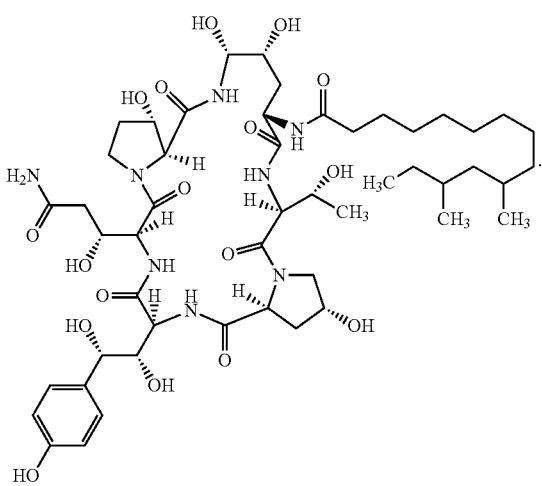

2

In the above method, the strong leaving-group compound is sulphydryl-substituted aromatic ring compound 4, wherein $R_1$ is selected from hydroxy, benzyloxy, phenoxy, or substituted phenoxy; $R_2$, $R_3$, $R_4$, $R_5$ is selected from hydrogen, C1-C6 alkyl, C1-C6 alkoxy, hydroxyl, or benzyloxyphenyl, substituted benzyloxyphenyl, nitro, fluorine, chlorine, bromine, iodine, respectively;

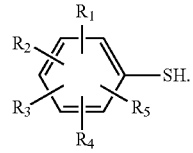

4

In a preferred example, in the sulphydryl-substituted aromatic ring compound 4, $R_1$ is selected from hydroxy, benzyloxy, phenoxy, or substituted phenoxy; $R_2$, $R_3$, $R_4$, $R_5$ is selected from hydrogen, C1-C4 alkyl, C1-C4 alkoxy, hydroxyl, bromine or nitro. More preferably, in the sulphydryl-substituted aromatic ring compound 4, $R_1$ is selected from hydroxy; $R_2$, $R_3$, $R_4$, $R_5$ is selected from hydrogen, methyl, or hydroxyl. Even more preferably, the sulphydryl-substituted aromatic ring compound 4 is selected from 4-hydroxy thiophenol.

In the above method, it is necessary to mix the strong leaving-group compound with an acid, wherein said acid is selected from trifluoroacetic acid, triflic acid, camphor sulfonic acid, methanesulfonic acid or p-toluene sulphonic acid; and the temperature for mixing is −50° C. to 40° C.; preferably, −20° C. to −15° C.

In the third aspect of the invention, the use of the compound of Formula 3 or the pharmaceutically acceptable salts thereof for preparing the compound of Formula 1 is provided;

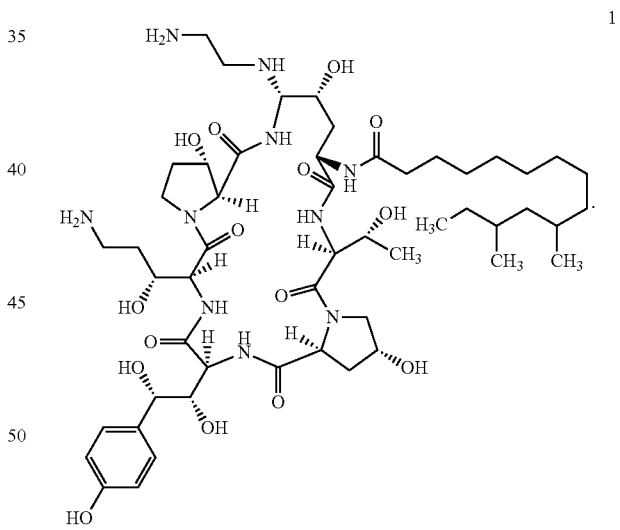

1

In the fourth aspect of the invention, the preparation method for the compound of Formula 1 is provided, said method comprising the following steps:

(a) mixing the compound of Formula 3 with ethylenediamine to obtain the compound of Formula 5; and (b) mixing the compound of Formula 5 with a hydroxyl protectant, and then with a borane complex to obtain the compound of Formula 1;

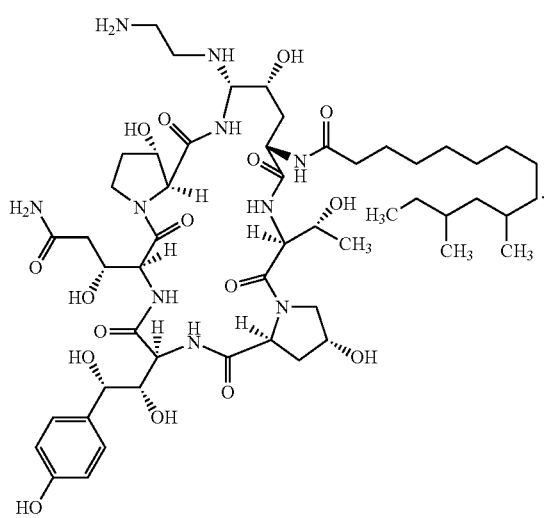

In the fifth aspect of the invention, the use of the compound of Formula 3 or the pharmaceutically acceptable salts thereof for preparing the medicaments for preventing or treating the diseases caused by fungi infection is provided.

In the sixth aspect of the invention, a pharmaceutical composition is provided, said composition comprising the compound of Formula 3 or the pharmaceutically acceptable salts thereof and pharmaceutically acceptable carriers.

Based on the above, a preparation method for caspofungin suitable for industrialization is provided.

DETAILED DESCRIPTION OF THE INVENTION

A new compound, i.e., the compound of Formula 3, and a simple preparation method for the compound of Formula 3 have been discovered by the inventors. Upon research, the inventors have discovered that the compound of Formula 1, i.e., caspofungin, can be readily obtained through aminolysis using ethylenediamine and reduction reaction.

As used herein, chemical formulae or names should include all of the optical isomers and stereoisomers, as well as the mixture or racemic mixture comprising the isomers.

Compound

The compound of Formula 3 is provided by the invention,

3

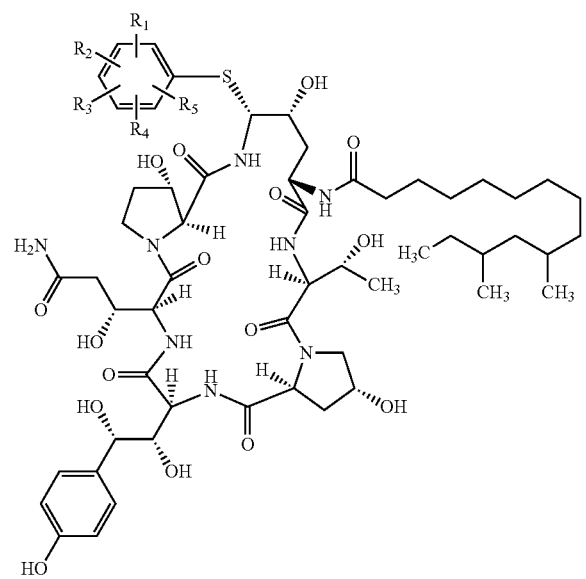

wherein $R_1$ is selected from hydroxy, benzyloxy, phenoxy, or substituted phenoxy, or substituted benzyloxy; $R_2$, $R_3$, $R_4$, $R_5$ is selected from hydrogen, C1-C6 alkyl, C1-C6 alkoxy, hydroxyl, or benzyloxyphenyl, substituted benzyloxyphenyl, nitro, fluorine, chlorine, bromine, iodine, respectively.

Generally, the compound provided by the invention is a mixture comprising stereoisomers, wherein one type of stereoisomer predominates. The preparation conditions can be regulated by a person skilled in the art using routine technical means to obtain the desired isomer. The compound, which is named as "normal" herein and in the preferred type of stereoisomer, is the compound in which the group at "C-5-orn" position is below the plane of said position, and the symbol "epi" can be used to designate the compound in which the group at "C-5-orn" position is over the plane of said position. "C-5-orn" position is determined as $5^{th}$ carbon in the 4-hydroxy ornithine moiety.

Preparation Method

A preparation method for the compound of Formula 3 is provided by the invention, comprising the following step:

mixing the compound of Formula 2 with a strong leaving-group compound to obtain the compound of Formula 3.

In the preparation method provided by the present invention, the starting material, i.e., the compound of Formula 2, can be obtained by the methods well-known in the art, for example (but not limited to), according to U.S. Pat. No. 5,021,341 (published on Jun. 4, 1991), culturing Zalerion arboricola ATCC 20868 in a medium rich in mannitol as the major carbon source.

In the present invention, the strong leaving-group compound is sulphydryl-substituted aromatic ring compound 4, wherein $R_1$ is selected from hydroxy, benzyloxy, phenoxy, substituted phenoxy, or substituted benzyloxy; $R_2$, $R_3$, $R_4$, $R_5$ is selected from hydrogen, C1-C6 alkyl, C1-C6 alkoxy, hydroxyl, or benzyloxyphenyl, substituted benzyloxyphenyl, nitro, fluorine, chlorine, bromine, iodine, respectively. Preferably, $R_1$ is selected from hydroxy, benzyloxy, phenoxy, or substituted phenoxy; $R_2$, $R_3$, $R_4$, $R_5$ is selected from hydrogen, C1-C4 alkyl, C1-C4 alkoxy, hydroxyl, bromine or nitro. More preferably, $R_1$ is selected from hydroxy; $R_2$, $R_3$, $R_4$, $R_5$ is selected from hydrogen, methyl, or hydroxyl. Most preferably, aromatic ring compound 4 is selected from 4-hydroxy thiophenol.

4

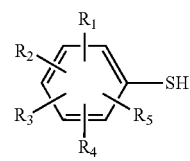

The acid can be any acid with moderate intensity, for example (but not limited to) trifluoroacetic acid, triflic acid, camphor sulfonic acid, methanesulfonic acid or p-toluene sulphonic acid; preferably, triflic acid.

In one example of the present invention, the reaction of the first step can be conducted by reacting the compound of Formula 2 with 4-hydroxy thiophenol dissolved in acetonitrile and trifluoroacetic acid to produce the hydroxyl-substituted diphenyl sulfide intermediate, i.e., the compound of Formula 3. The reaction liquid is neutralized by aqueous sodium acetate and the stable intermediate in solid can be obtained.

Use
An important use for the compound of Formula 3 is that it can be used as the intermediate for obtaining caspofungin, i.e., the compound of Formula 1. That is, aminolysis is applied to the compound of Formula 3 by using ethylenediamine to obtain the compound of Formula 5, and then the amide group in the compound of Formula 5 is reduced to amine group to obtain caspofungin.
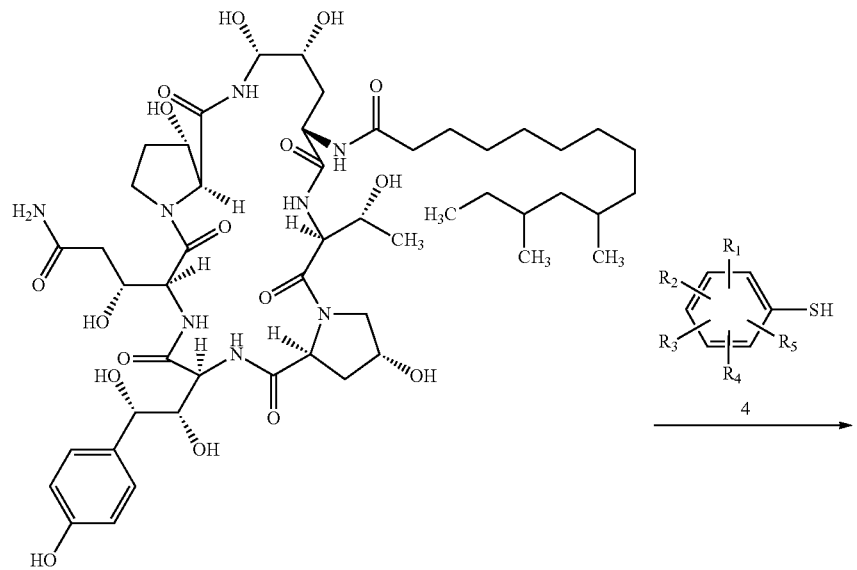
2
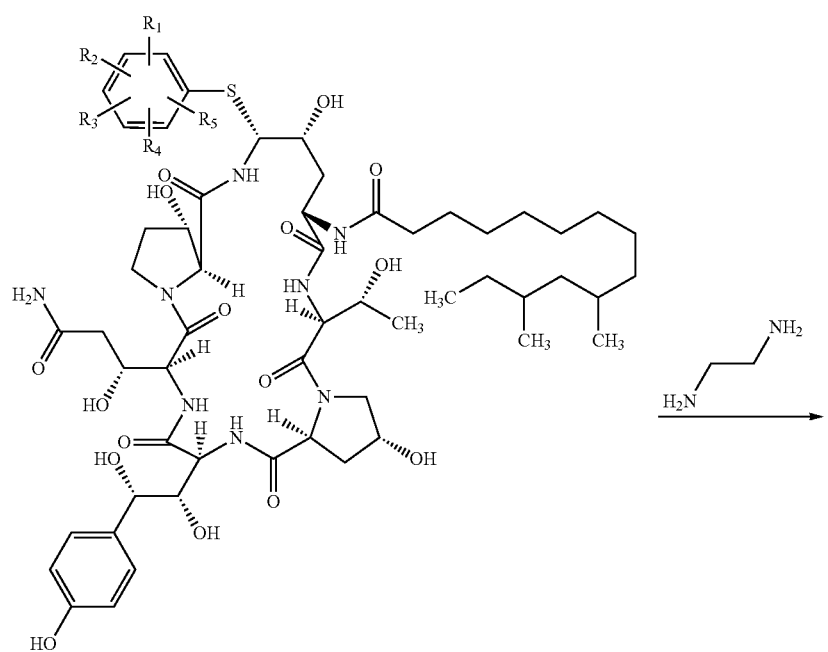
3

-continued

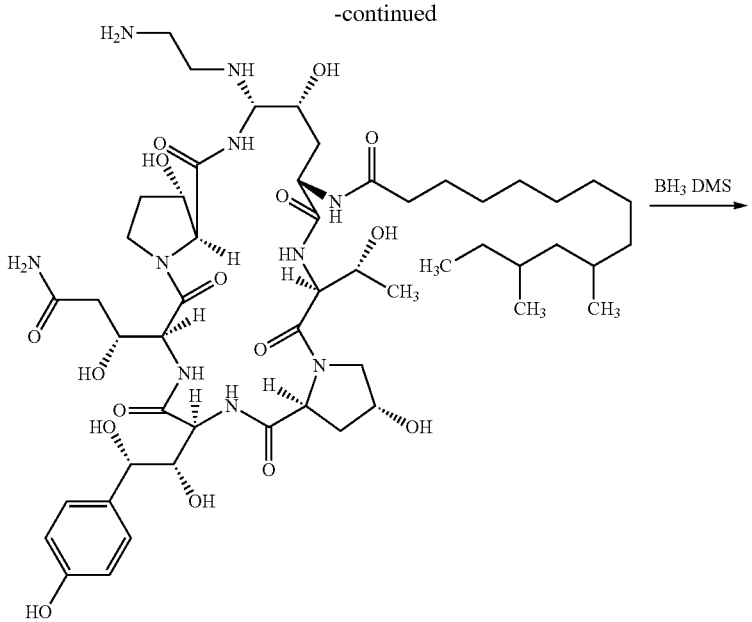

BH₃ DMS →

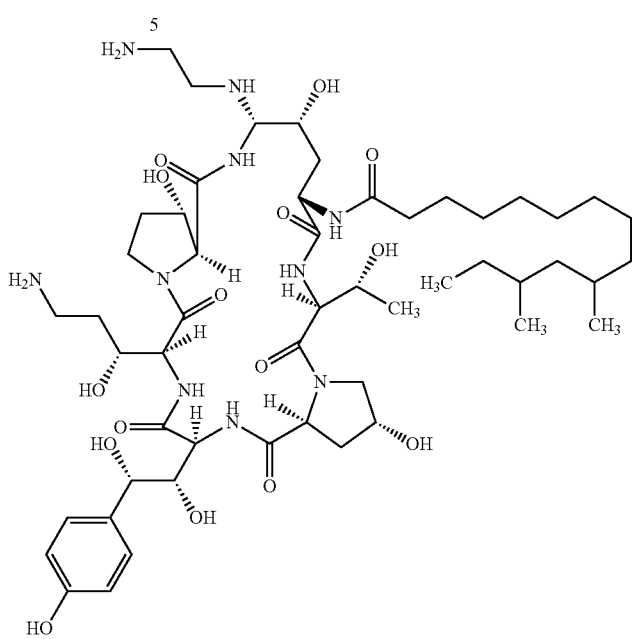

1

The compound of Formula 3, itself, can be used to efficiently treat fungus infections, treat or prevent the infection caused by *Candida* and *Aspergillus*, or prepare the medicaments for treating or preventing infectious diseases.

Therefore, a pharmaceutical composition comprising the compound of Formula 3 and pharmaceutically acceptable carriers can be provided by the invention.

As used herein, the term "efficient amount" refers to the carriers for the administration of therapeutics, including various excipients and diluents. The term refers to the carriers for therapeutics which themselves are not necessary active components and do not produce undue toxicity upon administration. Suitable carriers are well-known to a person skilled in the art. The detailed discussion about pharmaceutically acceptable excipients can be found in Remington's Pharmaceutical Sciences (Mack Pub. Co., N.J., 1991). The pharmaceutically acceptable excipient in a composition includes liquid, for example water, saline, glycerol and ethanol. Additionally, auxiliary agents, such as disintegrant, wetting agent, emulsifier, pH buffering agent, can be present in the carriers.

The pharmaceutical composition can be prepared into various dosage forms according to the different administration routes. The dosage form can be administrated through the following modes: oral, spray, rectum, nose, buccal, local, parenteral, such as subcutaneous, intravenous, intramuscle, intramuscular, intraperitoneal, intrathecal, intraventricular, intrasternum and intracranial injection or infusion, or by means of an explant depot.

All the features mentioned above or in the examples below of the invention can be optionally combined. All features disclosed in this specification may be used in any combination. Any alternative feature serving the same, equivalent, or similar purpose may replace each feature disclosed in this specification. Therefore, unless otherwise specified, the features as disclosed are only general examples of equivalent or similar features.

The main advantages of the invention include:
1. A new caspofungin analog is provided.
2. The present invention has many advantages, such as short synthesis route, mild reaction condition, and simple post-treatment. Additionally, thiophenol with odor and high toxicity is not used, thereby not polluting the environment or harming the operators, and the difficulty for operation and the requirement to the equipments are reduced, thereby significantly reducing the cost.
3. In the new preparation method for caspofungin analog provided by the invention, the compound of Formula 2 obtained by fermentation is used as the starting material, and the intermediates produced in the synthesis steps are stable, therefore, the quality of the final product can be controlled, thereby facilitating the industrialization.
4. The preparation method for the new caspofungin analog provided by the invention merely includes one step, the production is stable and high, and the compound can be readily synthesized.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

Example 1

Preparation of the Compound of Formula 3a from the Compound of Formula 2

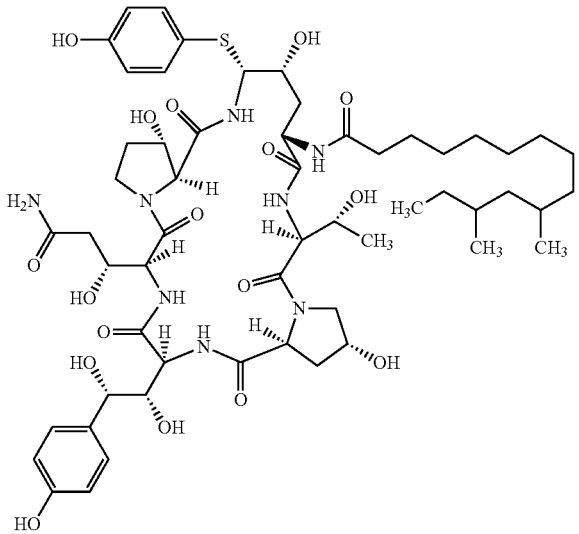

Under $N_2$, acetonitrile (30 ml), the compound of Formula 2 (1.0 g), phenyl boronic acid (0.12 g) and 4-hydroxy thiophenol (0.361 g) were mixed homogeneously. The reaction temperature was reduced to −20 to −15° C. Triflic acid (0.25 ml) was added dropwise. Upon addition, the reaction was conducted at −20 to −15° C. for about 2.5 h. The reaction was monitored by TLC. Upon completion, the reaction was quenched, and aqueous NaOAc (0.23 g NaOAc dissolved in 5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3a (0.93 g).

MS(ESI) 1173.6 (M+H$^+$), 1181.6 (M+Na$^+$);
$^1$H-NMR (500.13 MHz, CD$_3$OD) δ 7.45-7.35 (m, 2H), 7.15-7.05 (m, 2H), 6.8-6.7 (m, 4H), 5.38 (s, 1H), 5.05 (d, 1H), 4.94 (d, 1H), 4.57 (dd, 1H), 4.42-4.27 (m, 9H), 3.89 (m, 3H), 3.72 (m, 2H), 2.76 (dd, 1H), 2.45 (dd, 1H), 2.40 (m, 1H), 2.15-2.05 (m, 6H), 1.99 (m, 1H), 1.54 (m, 2H), 1.30-1.20 (m, 15H), 1.10 (d, 3H), 1.10-1.08 (m, 2H), 0.91 (t, 1H), 0.87-0.85 (t, 3H), 0.84, (d, 3H), 0.83 (d, 3H);
$^{13}$C-NMR (125 MHz, CD$_3$OD) 177.2, 175.7, 174.5, 173.7, 172.5, 172.0, 169.2, 158.7, 154.9, 131.0, 128.0, 123.0, 123.1, 116.1, 77.0, 76.2, 74.3, 71.6, 70.9, 70.5, 69.7, 68.2, 62.8, 61.5, 58.5, 57.3, 56.2, 55.5, 51.3, 49.8, 49.6, 49.4, 49.3, 49.1, 48.8, 48.7, 47.5, 47.0, 46.5, 40.0, 38.8, 38.3, 37.1, 36.0, 34.7, 33.1, 31.49, 31.45, 30.97, 30.94, 30.7 30.5, 28.2, 27.4, 21.0, 20.3, 19.6.

Example 2

Preparation of the Compound of Formula 5 from the Compound of Formula 3a

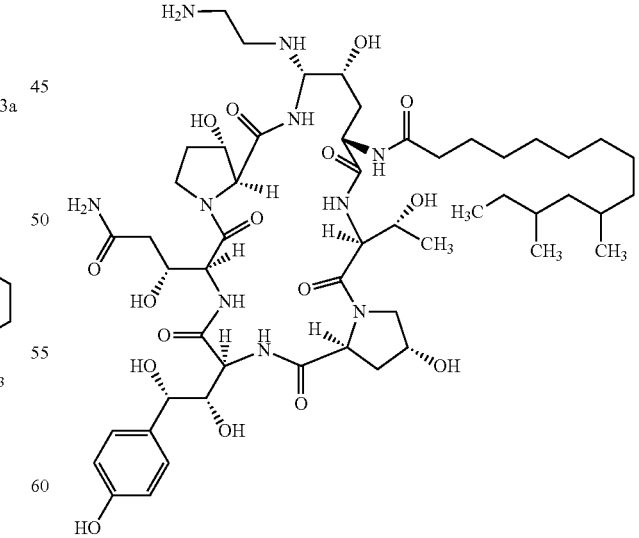

Under $N_2$, the compound of Formula 3a (2.0 g) was dissolved in methanol (8.5 ml), and the temperature of the solution was reduced to −20 to −15° C. Ethylenediamine (8.5 ml) was added dropwise. Upon addition, the temperature was increased to the room temperature, and the reaction was conducted for 48 h. The conversion rate for the reaction was 99% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 5 (1.70 g, the purity=95.0% by HPLC) in white solid. To the compound, methanol (8 ml) was added and the solution was agitated for dissolving the compound. Ethyl acetate (24 ml) was added dropwise at room temperature, and the resulting solution was agitated for 2 h at room temperature. The solution was cooled and filtered, and the resulting solid was dried to obtain the compound of Formula 5 (1.84 g).

MS(ESI): 1107.6 (M+H$^+$);

$^1$H-NMR (500.13 MHz, CD$_3$OD) δ 7.45-7.35 (m, 2H), 7.15-7.05 (m, 2H), 6.8-6.7 (m, 4H), 5.38 (s, 1H), 5.05 (d, 1H), 4.94 (d, 1H), 4.57 (dd, 1H), 4.42-4.27 (m, 9H), 3.89 (m, 3H), 3.72 (m, 2H), 2.65 (m, 2H); 2.45 (dd, 1H), 2.40 (m, 2H), 2.15-2.05 (m, 6H), 1.99 (m, 1H), 1.54 (m, 2H), 1.30-1.20 (m, 15H), 1.10 (d, 3H), 1.10-1.08 (m, 2H), 0.91 (t, 1H), 0.85-0.87 (t, 3H), 0.84, (d, 3H), 0.83 (d, 3H);

Example 3

Preparation of the Compound of Formula 1 from the Compound of Formula 5

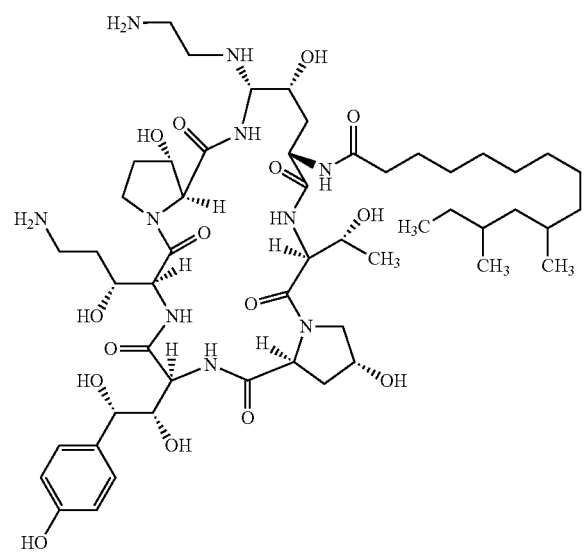

1

Under N$_2$, the compound of Formula 5 (1.0 g), phenyl boronic acid (0.14 g), anhydrous tetrahydrofuran (40 ml) were refluxed for 30 min. The reaction mixture was cooled to the room temperature, and BSTFA (1.06 ml) was added and the solution was agitated for 1 h at the room temperature. The reaction mixture was cooled to −10 to −5° C., and the complex of borane and dimethyl sulfide (0.4 ml, 0.94%) was added dropwise. Upon addition, the reaction mixture was warmed to 10 to 15° C., and the reaction was conducted for 3.5 h. The conversion rate for the reaction was 82% monitored by HPLC. Afterwards, 2 N hydrochloric acid (2.4 ml) was added dropwise, and water (80 ml) was added. The solvent was removed under the reduced pressure. Afterwards, the reaction mixture was agitated for 24 h at the room temperature. The reaction liquid was loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and lyophilized to obtain the caspofungin diacetate (0.75 g, the compound of Formula 1, the purity=98.0% by HPLC) in white solid.

MS(ESI): 1093.6 (M+H$^+$);

$^1$H-NMR (500.13 MHz, CD$_3$OD) δ 7.12 (m, 2H), 6.75 (m, 2H), 4.97 (d, 1H), 4.91 (d, 1H), 4.66 (d, 1H), 4.60 (dd, 3.2, 1H), 4.56-4.51 (m, 2H), 4.48 (dd, 1H), 4.32-4.28 (m, 3H) 4.22 (dd, 1H), 4.18 (d, 1H), 4.08-3.96 (m, 3H), 3.83 (m, 1H), 3.76 (d, 1H), 3.05 (t, 2H), 3.02-2.76 (m, 4H), 2.41 (dd, 1H), 2.29-2.17 (m, 3H) 2.11-1.78 (m, 5H), 1.90 (s, 6H), 1.58 (m, 2H), 1.53-1.19 (m, 15H), 1.16 (d, 3H), 1.13-1.00 (m, 2H), 0.91 (m, 1H), 0.87 (t, 3H), 0.85 (degenerated, 6H);

$^{13}$C-NMR (125 MHz, CD$_3$OD) 180.7, 176.7, 174.6, 171.1, 174.0, 173.3, 173.2, 169.4, 159.1, 116.7, 77.8, 76.1, 75.5, 72.5, 71.8, 70.6, 69.8, 64.8, 63.3, 58.9, 58.8, 57.6, 56.7, 56.5, 51.6, 47.5, 46.4, 44.5, 40.9, 39.5, 38.8, 38.5, 37.4, 36.2, 35.1, 33.4, 31.7, 31.6, 31.4, 31.3, 31.1, 30.84, 30.81, 28.5, 27.5, 24.8.

Example 4

Preparation of the Compound of Formula 3b from the Compound of Formula 2

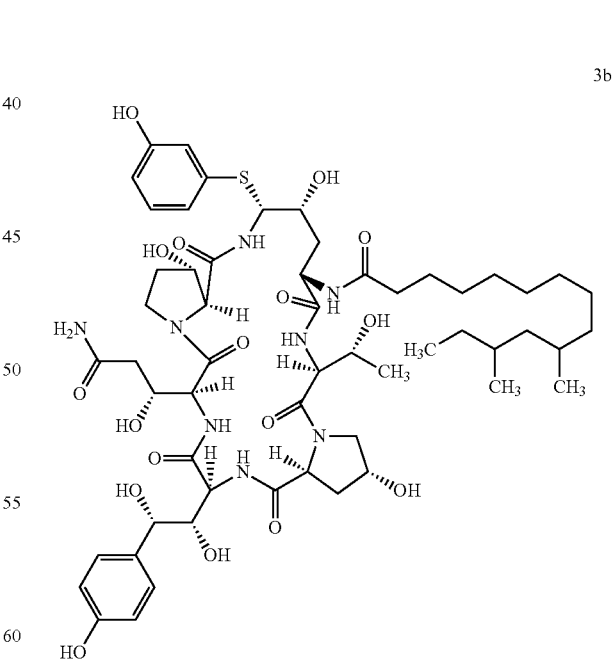

3b

Under N$_2$, acetonitrile (20 ml), the compound of Formula 2 (1.0 g), phenyl boronic acid (0.12 g) and 3-hydroxy thiophenol (0.40 g) were mixed homogeneously. The reaction temperature was reduced to −50 to −45° C. Trifluoroacetic acid (0.21 g) was added dropwise. Upon addition, the reaction was conducted at −50 to −45° C. for about 2.5 h. The reaction was monitored by TLC. Upon completion, the reaction was quenched, and aqueous NaOAc (0.23 g NaOAc dissolved in 5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3b (0.72 g).

MS(ESI) 1173.6 (M+H$^+$), 1195.6 (M+Na$^+$);

$^1$H-NMR (500.13 MHz, CD$_3$OD) δ7.2-7.10 (m, 3H), 6.9-6.7 (m, 5H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.76 (dd, 1H), 2.45 (dd, 1H), 2.40 (m, 1H), 2.15-2.05 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.87-0.85 (t, 3H), 0.84, (d, 3H), 0.83 (d, 3H);

$^{13}$C-NMR (125 MHz, CD$_3$OD) 177.2, 175.7, 174.5, 173.7, 172.5, 172.0, 169.2, 158.7, 158.5, 137.0, 133.0, 130.0, 129.6, 121.0, 116.2, 113.1, 112.1, 77.0, 76.2, 74.3, 71.6, 70.9, 70.5, 69.7, 68.2, 62.8, 61.5, 58.5, 57.3, 56.2, 55.5, 51.3, 49.8, 49.6, 49.4, 49.3, 49.1, 48.8, 48.7, 47.5, 47.0, 46.5, 40.0, 38.8, 38.3, 37.1, 36.0, 34.7, 33.1, 31.49, 31.45, 30.97, 30.94, 30.7 30.5, 28.2, 27.4, 21.0, 20.3, 19.6.

Example 5

Preparation of the Compound of Formula 3c from the Compound of Formula 2

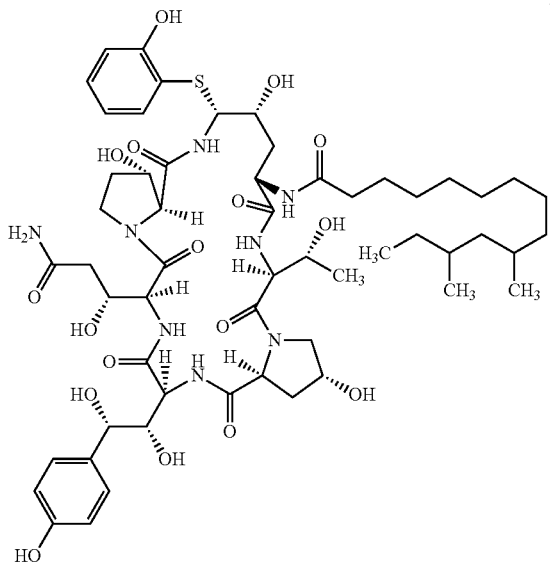

Under N$_2$, acetonitrile (20 ml), the compound of Formula 2 (1.0 g), phenyl boronic acid (0.14 g) and 2-hydroxy thiophenol (0.35 g) were mixed homogeneously. The reaction temperature was increased to 35 to 40° C. Methanesulfonic acid (0.27 g) was slowly added. Upon addition, the reaction was conducted for about 1.5 h at 35 to 40° C. The reaction was monitored by TLC. Upon completion, the reaction was quenched, and aqueous NaOAc (0.23 g NaOAc dissolved in 5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 4 h to obtain the compound of Formula 3c (0.75 g).

MS(ESI) 1173.6 (M+H$^+$), 1195.6 (M+Na$^+$);

$^1$H-NMR (500.13 MHz, CD$_3$OD) δ7.20-7.10 (m, 3H), 7.0-6.9 (m, 2H), 6.9-6.65 (m, 3H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.75 (dd, 1H), 2.45 (dd, 1H), 2.40 (m, 1H), 2.15-2.06 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.87-0.85 (t, 3H), 0.84, (d, 3H), 0.83 (d, 3H);

$^{13}$C-NMR (125 MHz, CD$_3$OD) 177.2, 175.7, 174.5, 173.7, 172.5, 172.0, 169.2, 158.7, 157.9, 133.0, 130.9, 129.6, 126.2, 116.2, 121.5, 120.7, 115.1, 77.0, 76.2, 74.3, 71.6, 70.9, 70.5, 69.7, 68.2, 62.8, 61.5, 58.5, 57.3, 56.2, 55.5, 51.3, 49.7, 49.6, 49.4, 49.3, 49.1, 48.8, 48.7, 47.5, 47.0, 46.5, 40.0, 38.8, 38.2, 37.1, 36.0, 34.7, 33.1, 31.49, 31.45, 30.96, 30.94, 30.7 30.5, 28.2, 27.4, 21.0, 20.3, 19.6.

Example 6

Preparation of the Compound of Formula 3d from the Compound of Formula 2

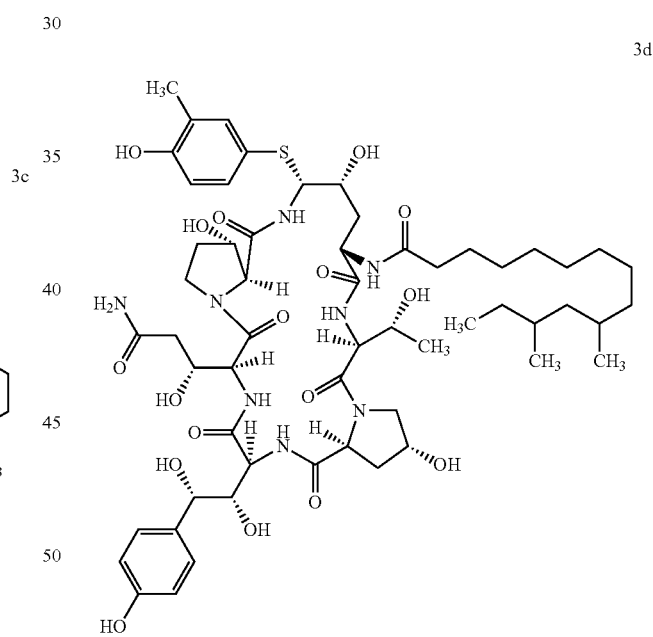

Under N$_2$, acetonitrile (30 ml), the compound of Formula 2 (1.0 g), phenyl boronic acid (0.23 g) and 4-hydroxy-3-methyl thiophenol (0.41 g) were mixed homogeneously. The reaction temperature was reduced to −50 to −45° C. Triflic acid (0.25 ml) was added dropwise. Upon addition, the reaction was conducted for about 1 h at −50 to −45° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the reaction solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3d (0.75 g).

MS(ESI) 1187.6 (M+H⁺);

¹H-NMR (500.13 MHz, CD₃OD) δ7.20-7.15 (m, 3H), 7.0-6.9 (m, 1H), 6.7-6.6 (m, 3H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.75 (dd, 1H), 2.45 (dd, 1H), 2.40 (m, 1H), 2.20 (s, 3H), 2.15-2.06 (m, 6H), 1.97 (m, 1H), 1.54 (m, 2H), 1.30-1.20 (m, 15H), 1.10 (d, 3H), 1.10-1.08 (m, 2H), 0.91 (t, 1H), 0.88-0.85 (t, 3H), 0.84, (d, 3H), 0.83 (d, 3H);

¹³C-NMR (125 MHz, CD₃OD) 177.2, 175.7, 174.5, 173.7, 172.5, 172.0, 169.2, 158.7, 150.9, 133.0, 129.6, 128.9, 128.0, 126.3, 125.1, 116.0, 77.0, 76.2, 74.3, 71.6, 70.9, 70.5, 69.7, 68.2, 62.7, 61.5, 58.5, 57.3, 56.2, 55.5, 51.3, 49.8, 49.6, 49.4, 49.3, 49.1, 48.8, 48.7, 47.5, 47.0, 46.5, 40.0, 38.8, 38.4, 37.1, 36.0, 34.7, 33.1, 31.48, 31.45, 30.97, 30.94, 30.6 30.5, 28.2, 27.4, 21.0, 20.3, 19.6. 14.8.

Example 7

Preparation of the Compound of Formula 3e from the Compound of Formula 2

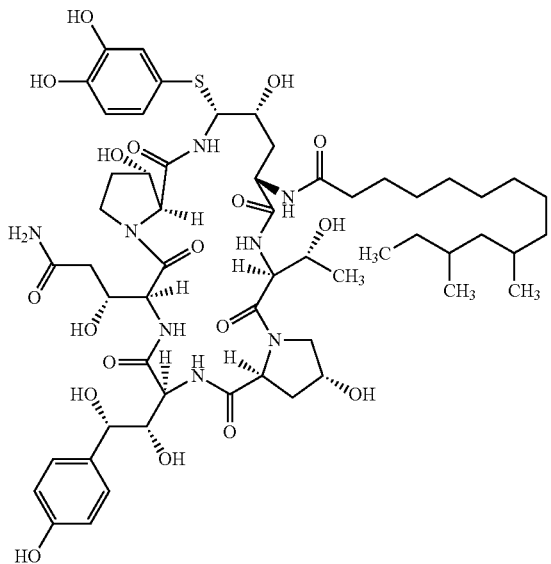

Under N₂, acetonitrile (30 ml), the compound of Formula 2 (1.0 g), phenyl boronic acid (0.23 g) and 3,4-dihydroxy thiophenol (0.42 g) were mixed homogeneously. The reaction temperature was reduced to below −20 to −15° C. Triflic acid (0.25 ml) was added dropwise. Upon addition, the reaction was conducted for about 2.5 h at −20 to −15° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3e (0.70 g).

MS(ESI) 1189.6 (M+H⁺); 1211.6 (M+Na⁺);

¹H-NMR (500.13 MHz, CD₃OD) δ7.20-7.15 (m, 2H), 6.75-6.6 (m, 4H), 6.45 (m, 1H), 5.38 (s, 1H), 5.06 (d, 1H), 4.94 (d, 1H), 4.57 (dd, 1H), 4.42-4.28 (m, 9H), 3.89 (m, 3H), 3.72 (m, 2H), 2.75 (dd, 1H), 2.45 (dd, 1H), 2.40 (m, 1H), 2.15-2.06 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.88-0.85 (t, 3H), 0.84, (d, 3H), 0.83 (d, 3H);

¹³C-NMR (125 MHz, CD₃OD) 177.2, 175.7, 174.5, 173.7, 172.5, 172.0, 169.2, 158.7, 147.5, 143.7, 133.0, 130.4, 129.6, 123.6, 117.5, 116.2, 114.5, 77.0, 76.2, 74.3, 71.6, 70.9, 70.5, 69.7, 68.2, 62.8, 61.5, 58.5, 57.3, 56.2, 55.5, 51.3, 49.8, 49.6, 49.4, 49.3, 49.1, 48.8, 48.7, 47.5, 47.0, 46.5, 40.0, 38.8, 38.3, 37.1, 36.0, 34.7, 33.1, 31.49, 31.45, 30.97, 30.94, 30.7 30.5, 28.2, 27.4, 21.0, 20.3, 19.6.

Example 8

Preparation of the Compound of Formula 3f from the Compound of Formula 2

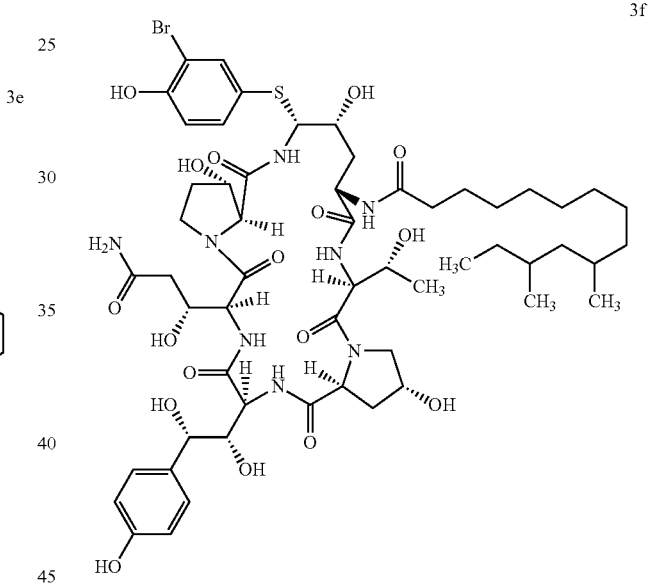

Under N₂, acetonitrile (30 ml), the compound of Formula 2 (1.0 g), phenyl boronic acid (0.23 g) and 3-bromo4-hydroxy thiophenol (0.59 g) were mixed homogeneously. The reaction temperature was reduced to −10 to −5° C. Triflic acid (0.25 ml) was added dropwise. Upon addition, the reaction was conducted for about 2.5 h at −10 to −5° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3f (0.97 g).

MS(ESI) 1273.5 (M+Na⁺);

¹H-NMR (500.13 MHz, CD₃OD) δ 7.45-7.35 (m, 2H), 7.15-7.05 (m, 2H), 6.8-6.7 (m, 3H), 5.37 (s, 1H), 5.04 (d, 1H), 4.94 (d, 1H), 4.57 (dd, 1H), 4.42-4.27 (m, 9H), 3.89 (m, 3H), 3.72 (m, 2H), 2.76 (dd, 1H), 2.46 (dd, 1H), 2.40 (m, 1H), 2.15-2.06 (m, 6H), 1.99 (m, 1H), 1.54 (m, 2H), 1.30-1.21 (m, 15H), 1.10 (d, 3H), 1.10-1.08 (m, 2H), 0.91 (t, 1H), 0.87-0.85 (t, 3H), 0.85, (d, 3H), 0.83 (d, 3H);

$^{13}$C-NMR (125 MHz, CD$_3$OD) 177.2, 175.7, 174.5, 173.7, 172.5, 172.0, 169.2, 156.7, 154.9, 133.4, 131.0, 130.0, 126.3, 118.3, 114.1, 77.0, 76.2, 74.3, 71.6, 70.9, 70.6, 69.7, 68.2, 62.8, 61.5, 58.5, 57.3, 56.2, 55.5, 51.3, 49.8, 49.6, 49.4, 49.3, 49.1, 48.8, 48.7, 47.5, 47.0, 46.5, 40.0, 38.8, 38.3, 37.1, 36.0, 34.8, 33.1, 31.49, 31.45, 30.97, 30.94, 30.7 30.5, 28.2, 27.4, 21.0, 20.4, 19.6.

Example 9

Preparation of the Compound of Formula 3g from the Compound of Formula 2

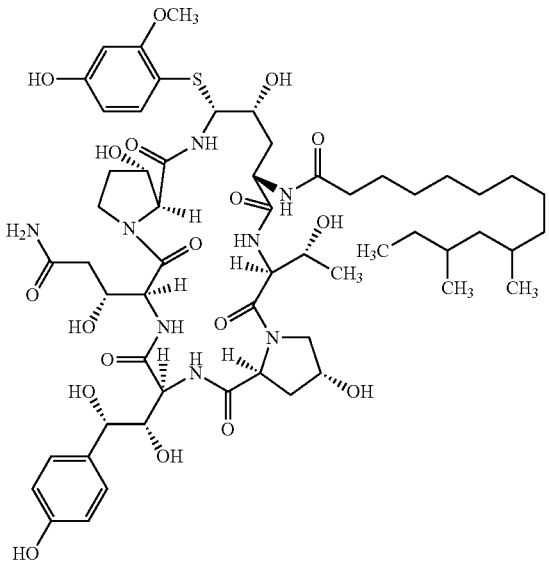

3g

Under N$_2$, acetonitrile (30 ml), the compound of Formula 2 (1.0 g), phenyl boronic acid (0.23 g) and 4-hydroxy-2-methoxy thiophenol (0.45 g) were mixed homogeneously. The reaction temperature was reduced to below −20 to −15° C. Triflic acid (0.25 ml) was added dropwise. Upon addition, the reaction was conducted for about 2.5 h at −20 to −15° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3g (0.98 g).

MS(ESI) 1203.6 (M+H$^+$), 1225.6 (M+Na$^+$);

$^1$H-NMR (500.13 MHz, CD$_3$OD) δ 7.45-7.35 (m, 2H), 7.19-7.08 (m, 1H), 6.8-6.7 (m, 4H), 5.38 (s, 1H), 5.05 (d, 1H), 4.94 (d, 1H), 4.57 (dd, 1H), 4.43-4.27 (m, 9H), 3.90 (m, 3H), 3.80 (s, 3H), 3.72 (m, 2H), 2.76 (dd, 1H), 2.45 (dd, 1H), 2.40 (m, 1H), 2.15-2.05 (m, 6H), 1.99 (m, 1H), 1.56 (m, 2H), 1.30-1.20 (m, 15H), 1.10 (d, 3H), 1.10-1.09 (m, 2H), 0.91 (t, 1H), 0.88-0.85 (t, 3H), 0.84, (d, 3H), 0.83 (d, 3H);

$^{13}$C-NMR (125 MHz, CD$_3$OD) 177.2, 175.7, 174.5, 173.7, 172.5, 172.0, 159.2, 158.7, 157.2, 131.0, 128.0, 117.7, 129.2, 116.1, 102.2, 77.0, 76.2, 74.3, 71.5, 70.9, 70.5, 69.7, 68.2, 62.8, 61.5, 58.5, 57.3, 56.2, 55.5, 55.3, 51.3, 49.8, 49.6, 49.4, 49.4, 49.1, 48.8, 48.7, 47.5, 47.0, 46.5, 40.0, 38.9, 38.3, 37.1, 36.0, 34.7, 33.1, 31.49, 31.45, 30.97, 30.94, 30.7 30.4, 28.2, 27.5, 21.0, 20.3, 19.6.

Example 10

Preparation of the Compound of Formula 3h from the Compound of Formula 2

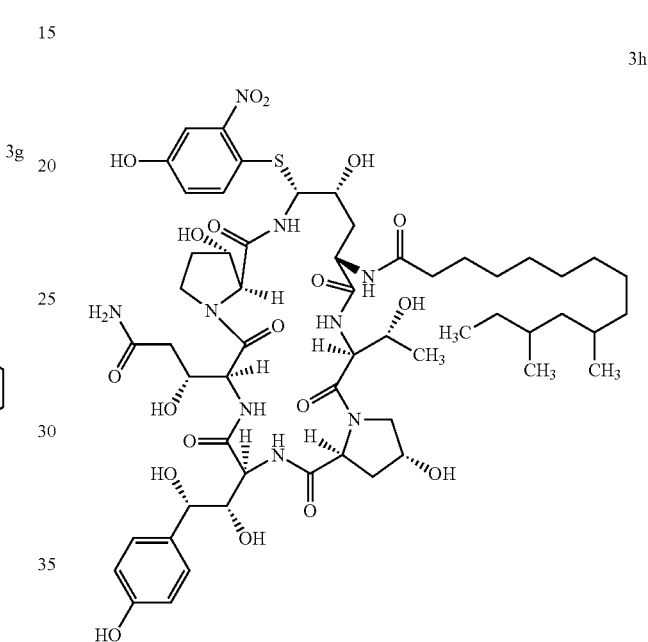

3h

Under N$_2$, acetonitrile (30 ml), the compound of Formula 2 (1.0 g), phenyl boronic acid (0.23 g) and 4-hydroxy-2-nitrothiophenol (0.49 g) were mixed homogeneously. The reaction temperature was reduced to 0 to 5° C. Triflic acid (0.25 ml) was added dropwise. Upon addition, the reaction was conducted for about 2.5 h at 0 to 5° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3h (0.94 g).

MS(ESI) 1218.6 (M+H$^+$);

$^1$H-NMR (500.13 MHz, CD$_3$OD) δ 7.68-7.48 (m, 2H), 7.19-7.15 (m, 2H), 6.8-6.7 (m, 3H), 5.38 (s, 1H), 5.05 (d, 1H), 4.94 (d, 1H), 4.57 (dd, 1H), 4.42-4.27 (m, 9H), 3.89 (m, 3H), 3.72 (m, 2H), 2.76 (dd, 1H), 2.45 (dd, 1H), 2.41 (m, 1H), 2.15-2.05 (m, 6H), 1.99 (m, 1H), 1.56 (m, 2H), 1.30-1.20 (m, 15H), 1.10 (d, 3H), 1.10-1.08 (m, 2H), 0.93 (t, 1H), 0.87-0.85 (t, 3H), 0.84, (d, 3H), 0.83 (d, 3H);

$^{13}$C-NMR (125 MHz, CD$_3$OD) 177.2, 175.7, 174.5, 173.7, 172.5, 172.0, 159.2, 157.2, 148.7, 131.0, 129.3, 128.0, 127.2, 117.7, 116.1, 111.7, 77.0, 76.2, 74.3, 71.6, 70.9, 70.5, 69.8, 68.2, 62.8, 61.5, 58.5, 57.3, 56.2, 55.6, 51.3, 49.8, 49.6, 49.4, 49.3, 49.1, 48.8, 48.7, 47.5, 47.1, 46.5, 40.0, 38.8, 38.3, 37.2, 36.0, 34.7, 33.1, 31.49, 31.46, 30.97, 30.94, 30.7 30.5, 28.3, 27.4, 21.0, 20.3, 19.6.

Example 11

Preparation of the Compound of Formula 3i from the Compound of Formula 2

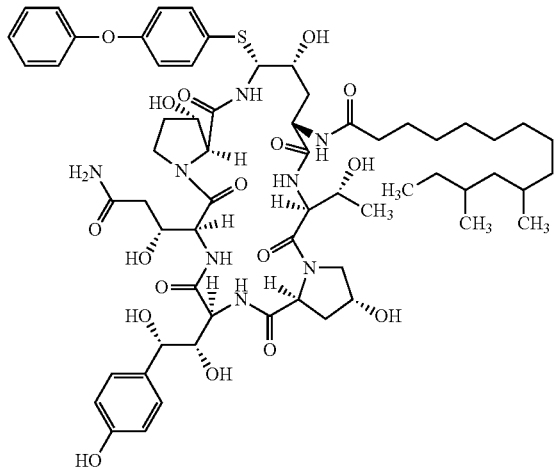

3i

Under $N_2$, acetonitrile (30 ml), the compound of Formula 2 (1.0 g), phenyl boronic acid (0.23 g) and 4-phenoxy thiophenol (0.58 g) were mixed homogeneously. The reaction temperature was reduced to below 35 to 40° C. Triflic acid (0.25 ml) was added dropwise. Upon addition, the reaction was conducted for about 2.5 h at 35 to 40° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3i (1.05 g).

MS(ESI) 1249.6 (M+H$^+$), 1271.6 (M+Na$^+$);

$^1$H-NMR (500.13 MHz, CD$_3$OD) δ 7.45-7.35 (m, 4H), 7.30-7.25 (m, 2H), 7.15-7.05 (m, 5H), 6.8-6.7 (m, 2H), 5.38 (s, 1H), 5.05 (d, 1H), 4.96 (d, 1H), 4.57 (dd, 1H), 4.42-4.28 (m, 9H), 3.89 (m, 3H), 3.72 (m, 2H), 2.76 (dd, 1H), 2.47 (dd, 1H), 2.40 (m, 1H), 2.15-2.06 (m, 6H), 1.99 (m, 1H), 1.54 (m, 2H), 1.30-1.21 (m, 15H), 1.10 (d, 3H), 1.10-1.08 (m, 2H), 0.91 (t, 1H), 0.88-0.86 (t, 3H), 0.84, (d, 3H), 0.83 (d, 3H);

$^{13}$C-NMR (125 MHz, CD$_3$OD) 177.2, 175.7, 174.5, 173.7, 172.5, 172.0, 169.2, 157.7, 153.9, 133.4, 129.3, 128.0, 121.8, 118.9, 116.7, 77.0, 76.2, 74.3, 71.6, 70.9, 70.6, 69.7, 68.2, 62.8, 61.5, 58.5, 57.3, 56.2, 55.5, 51.3, 49.8, 49.6, 49.4, 49.3, 49.1, 48.9, 48.7, 47.5, 47.0, 46.5, 40.0, 38.8, 38.4, 37.1, 36.0, 34.7, 33.1, 31.49, 31.45, 30.97, 30.94, 30.7 30.5, 28.2, 27.4, 21.0, 20.3, 19.7.

Example 12

Preparation of the Compound of Formula 3j from the Compound of Formula 2

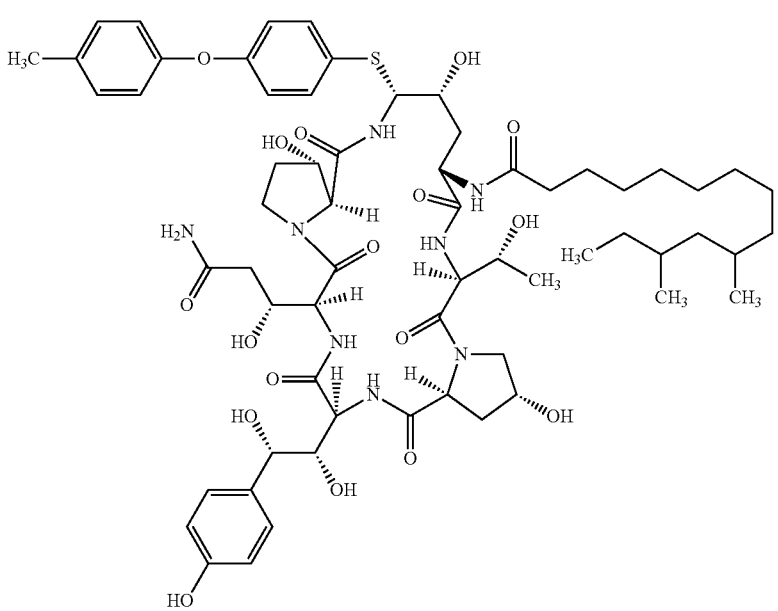

3j

Under $N_2$, acetonitrile (30 ml), the compound of Formula 2 (1.0 g), phenyl boronic acid (0.23 g) and 4-p-methylphenoxy thiophenol (0.62 g) were mixed homogeneously. The reaction temperature was reduced to 25 to 30° C. Triflic acid (0.25 ml) was added dropwise. Upon addition, the reaction was conducted for about 2.5 h at 25 to 30° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3j (1.05 g).

MS(ESI) 1263.6 (M+H$^+$);

$^1$H-NMR (500.13 MHz, CD$_3$OD) δ7.35-7.25 (m, 4H), 7.20-7.05 (m, 4H), 6.8-6.7 (m, 4H), 5.38 (s, 1H), 5.05 (d, 1H), 4.96 (d, 1H), 4.57 (dd, 1H), 4.42-4.28 (m, 9H), 3.89 (m, 3H), 3.72 (m, 2H), 2.76 (dd, 1H), 2.47 (dd, 1H), 2.40 (m, 1H), 2.34 (d, 3H), 2.15-2.06 (m, 6H), 1.99 (m, 1H), 1.54 (m, 2H), 1.30-1.21 (m, 15H), 1.10 (d, 3H), 1.10-1.08 (m, 2H), 0.91 (t, 1H), 0.88-0.86 (t, 3H), 0.84, (d, 3H), 0.83 (d, 3H);

$^{13}$C-NMR (125 MHz, CD$_3$OD) 177.2, 175.7, 174.5, 173.7, 172.5, 172.0, 169.2, 153.9, 153.5, 133.4, 131.5, 129.3, 128.0, 117.7, 116.0, 77.0, 76.2, 74.3, 71.6, 70.9, 70.6, 69.7, 68.2, 62.8, 61.5, 58.5, 57.3, 56.2, 55.5, 51.3, 49.9, 49.6, 49.4, 49.3, 49.1, 48.9, 48.7, 47.6, 47.0, 46.5, 40.0, 38.8, 38.3, 37.1, 36.0, 34.7, 33.1, 31.47, 31.45, 30.97, 30.94, 30.7 30.5, 28.3, 27.4, 21.3, 21.0, 20.3, 19.7.

Example 13

Preparation of the Composition Comprising the Compound of Formula 3a

| Component | Amount |
|---|---|
| The compound of Formula 3a | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 3a was added, wherein the amount of the compound in the resulting solution is 42 mg/ml. The mixed solution was agitated, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

Example 14

Preparation of the Composition Comprising the Compound of Formula 3b

| Component | Amount |
|---|---|
| The compound of Formula 3b | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 3b was added, wherein the amount of the compound in the resulting solution is 42 mg/ml. The mixed solution was agitated, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

Example 15

Preparation of the Composition Comprising the Compound of Formula 3c

| Component | Amount |
|---|---|
| The compound of Formula 3c | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 3c was added, wherein the amount of the compound in the resulting solution is 42 mg/ml. The mixed solution was agitated, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

Example 16

Preparation of the Composition Comprising the Compound of Formula 3d

| Component | Amount |
|---|---|
| The compound of Formula 3d | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 3d was added, wherein the amount of the compound in the resulting solution is 42 mg/ml. The mixed solution was agitated, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:

1. The compound of Formula 3 or the pharmaceutically acceptable salts thereof,

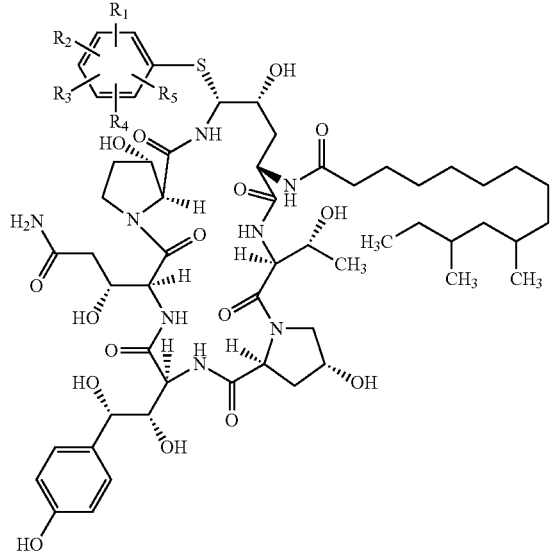

3 wherein $R_1$ is selected from hydroxy, benzyloxy, phenoxy, substituted phenoxy, or substituted benzyloxy; and $R_2$, $R_3$, $R_4$, and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine.

2. The compound according to claim 1, wherein $R_1$ is selected from hydroxy, benzyloxy, phenoxy, or substituted phenoxy; and $R_2$, $R_3$, $R_4$, and $R_5$ are selected from hydrogen, C1-C4 alkyl, C1-C4 alkoxy, hydroxyl, bromine or nitro.

3. The compound according to claim 2, wherein $R_1$ is selected from hydroxy; and $R_2$, $R_3$, $R_4$, and $R_5$ are selected from hydrogen, methyl, or hydroxyl.

4. The compound according to claim 3, wherein the compound is the compound of Formula 3a, 3b, 3c, 3d, or 3e:

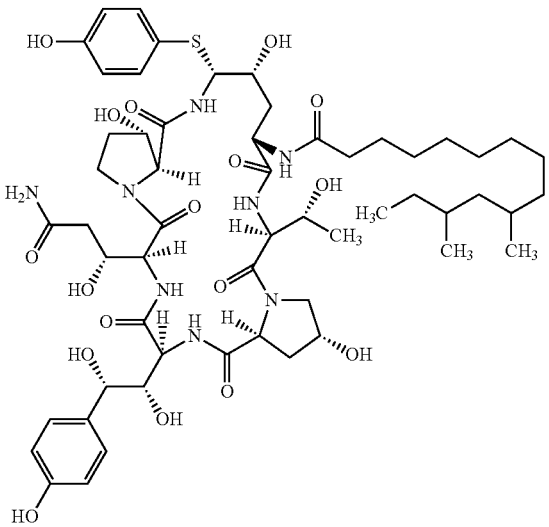

3a

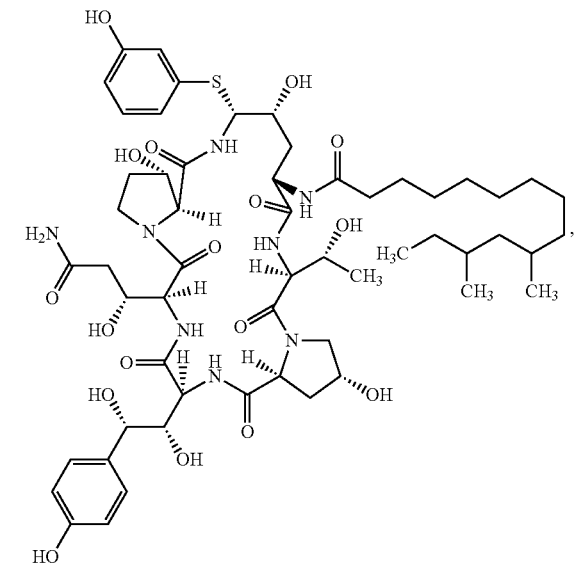

3b

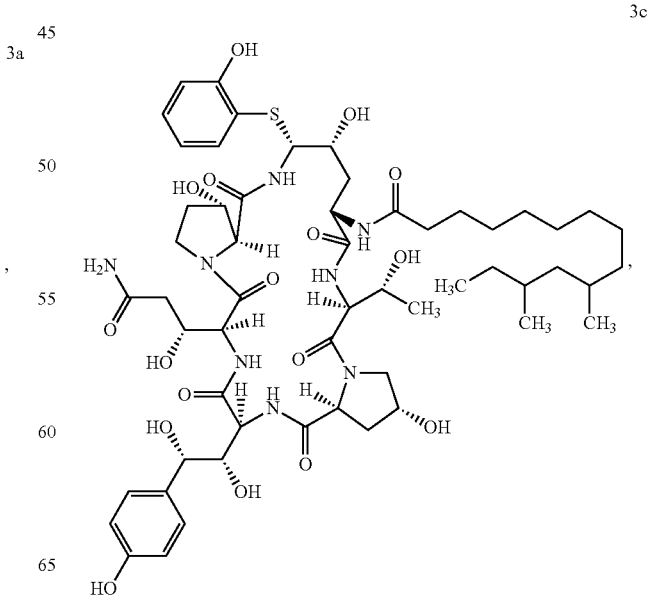

3c

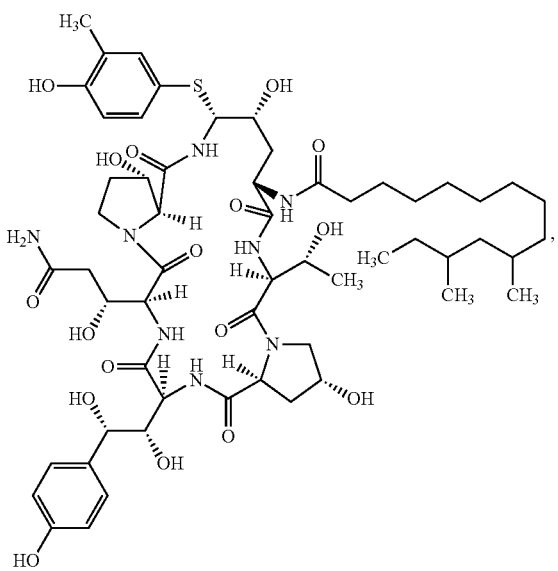

3d

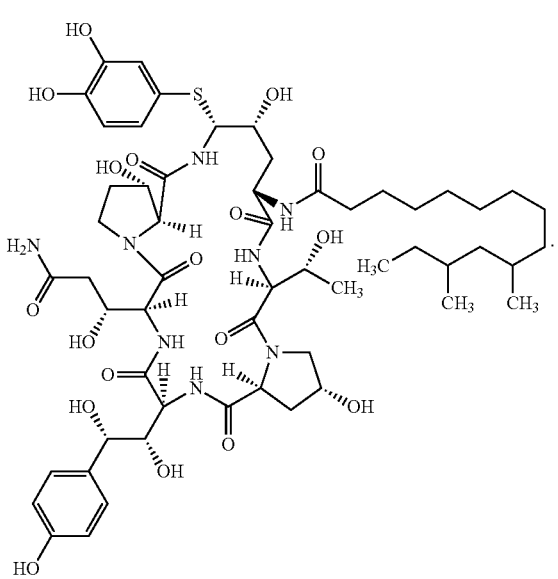

3e

5. The compound according to claim 4, wherein the compound is the compound of Formula 3a.

6. A preparation method for the compound according to claim 1, wherein said method comprises the following step:
 mixing the compound of Formula 2 with a strong leaving-group compound, thereby obtaining the compound of Formula 3 according to claim 1,

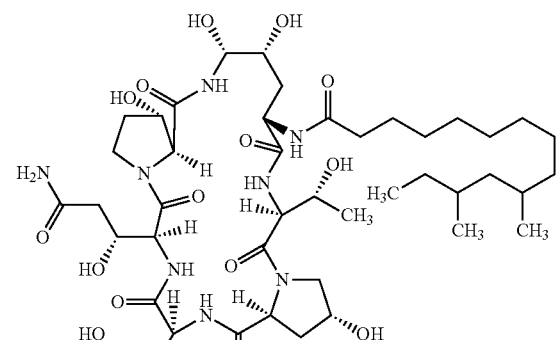

2

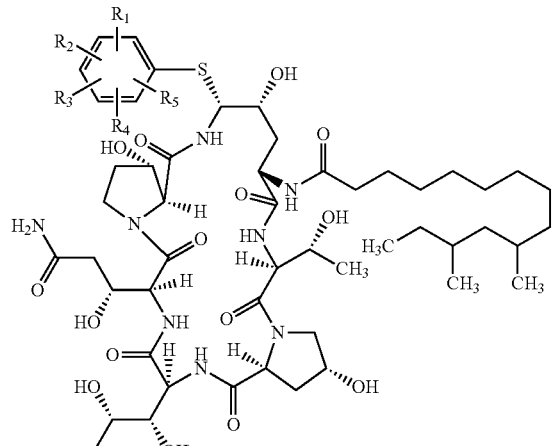

3

7. The preparation method according to claim 6, wherein the strong leaving-group compound is a sulphydryl-substituted aromatic ring compound 4, wherein $R_1$ is selected from hydroxy, benzyloxy, phenoxy, substituted phenoxy, or substituted benzyloxy; and $R_2$, $R_3$, $R_4$, and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine;

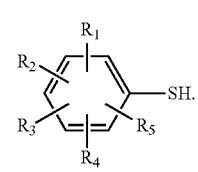

4

8. The preparation method according to claim 7, wherein in the sulphydryl-substituted aromatic ring compound 4, $R_1$ is selected from hydroxy, benzyloxy, phenoxy, or substituted phenoxy; and R₂, R₃, R₄, and R₅ are selected from hydrogen, C1-C4 alkyl, C1-C4 alkoxy, hydroxyl, bromine or nitro.

9. The preparation method according to claim 8, wherein in the sulphydryl-substituted aromatic ring compound 4, R₁ is selected from hydroxy; and R₂, R₃, R₄, and R₅ are selected from hydrogen, methyl, or hydroxyl.

10. The preparation method according to claim 9, wherein the sulphydryl-substituted aromatic ring compound 4 is 4-hydroxy thiophenol.

11. The preparation method according to claim 6, wherein the strong leaving-group compound is mixed with an acid, wherein said acid is selected from trifluoroacetic acid, triflic acid, camphor sulfonic acid, methanesulfonic acid or p-toluene sulphonic acid.

12. The preparation method according to claim 6, wherein the temperature for mixing is −50° C. to 40° C.

13. The compound according to claim 1 used for preparing the compound of Formula 1;

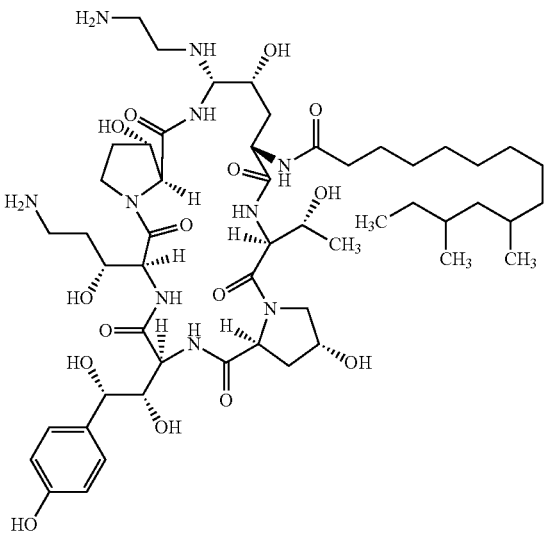

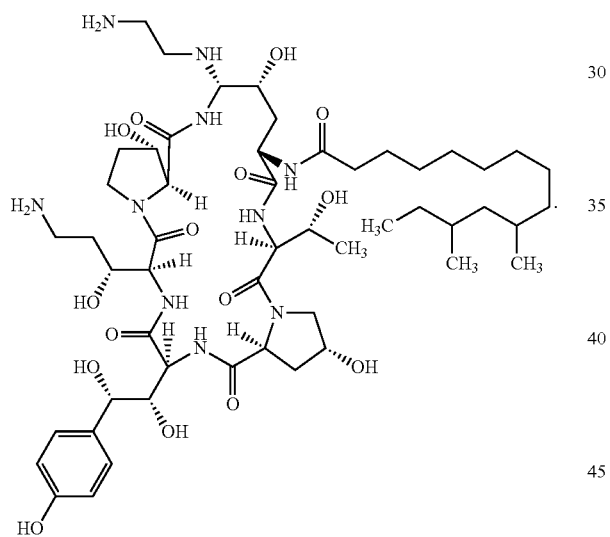

14. A preparation method for the compound of Formula 1, wherein said
method comprises the following steps:
(a) mixing the compound of Formula 3 with ethylenediamine to obtain the compound of Formula 5; and
(b) mixing the compound of Formula 5 with a hydroxyl protectant, and then with a borane complex to obtain the compound of Formula 1;

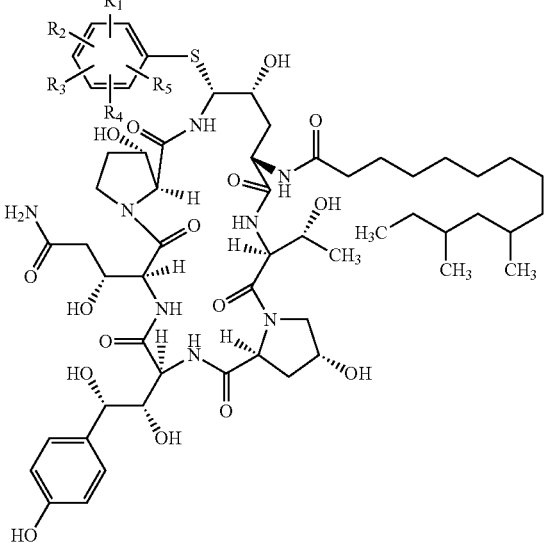

-continued

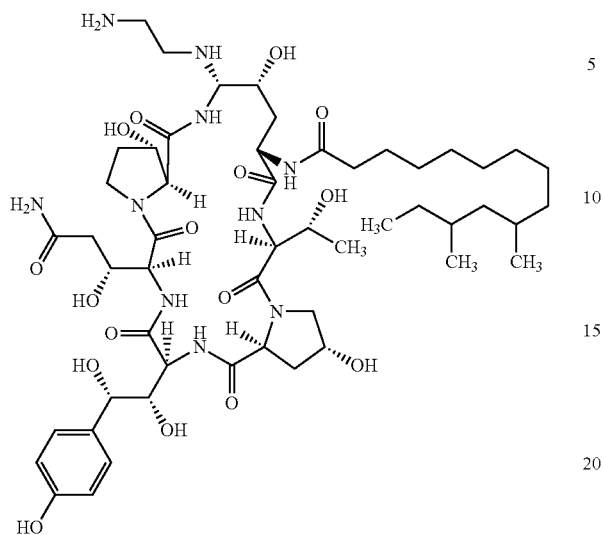

wherein R₁ is selected from hydroxy, benzyloxy, phenoxy, substituted phenoxy, or substituted benzyloxy; and $R_2$, $R_3$, $R_4$ and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine.

15. The preparation method according to claim 6, wherein the temperature for mixing is −20° C. to −15° C.

* * * * *